United States Patent
Katou et al.

(10) Patent No.: US 6,222,049 B1
(45) Date of Patent: Apr. 24, 2001

(54) 2-(ω-ALKOXYCARBONYL ALKANOYL)-4-BUTANOLIDE

(75) Inventors: Tetsuya Katou; Go Hata, both of Kanagawa; Takeaki Etoh; Nobuhiko Ito, both of Chiba, all of (JP)

(73) Assignees: Toray Industries; Soda Aromatic Co., Ltd., both of (JP)

( * ) Notice: Subject to any disclaimer, the term of this patent is extended or adjusted under 35 U.S.C. 154(b) by 56 days.

(21) Appl. No.: 09/103,324

(22) Filed: Jun. 23, 1998

Related U.S. Application Data

(62) Division of application No. 08/809,751, filed on Apr. 30, 1997, now Pat. No. 5,808,106.

(30) Foreign Application Priority Data

Aug. 4, 1995 (WO) .................................... PCT/JP95/01555

(51) Int. Cl.$^7$ .................................... C07D 307/58
(52) U.S. Cl. ............................................. 549/322
(58) Field of Search ................................. 549/322

(56) References Cited

U.S. PATENT DOCUMENTS 5,023,351    6/1991  Yoshida et al. .................. 549/321
5,693,828  * 12/1997  Belko ................................ 549/266

OTHER PUBLICATIONS

Ohloff, Scent and Fragrances, Springer–Verlag, Berlin, New York, etc., pp. 180, 181, 202, 203, 210 and 211, 1990.*

Chemical Materials, Part 2 (An–ei–hou) (published Jan. 24, 1994) Serial No. 12463 of Gazette, p. 863. ISBN: 4-87326-146-5 C2543.

* cited by examiner

*Primary Examiner*—Bernard Dentz
(74) *Attorney, Agent, or Firm*—Austin R. Miller

(57) ABSTRACT

2-(ω-alkoxycarbonyl alkanoyl)-4-butanolide is produced with a high selectivity and yield through condensation reaction of Y-butyrolactone with a readily available, low-price dicarboxylate as represented by the following general formula:

$$ROOC(CH_2)_nCOOR$$

wherein n denotes an integer of 8–13, and R denotes an alkyl group or an alkenyl group.

6 Claims, No Drawings

2-(ω-ALKOXYCARBONYL ALKANOYL)-4-BUTANOLIDE

This application is a divisional of application Ser. No. 08/809,751, filed Apr. 30, 1997 now U.S. Pat. No. 5,808,106, incorporated herein by reference.

TECHNICAL FIELD

The present invention relates to a method for producing 2-(ω)-alkoxycarbonyl alkanoyl)-4-butanolide and a long-chain ω-hydroxycarboxylic acid

BACKGROUND OF THE INVENTION

A macrocyclic lactone can be derived from a long-chain ω-hydroxycarboxylic acid through intramolecular cyclization. Such macrocyclic lactones as cyclopentadecanolide and cyclohexadecanolide are important materials for preparing musk odor. It is known that 2-(ω-alkoxycarbonyl alkanoyl)-4-butanolide can be converted into a long-chain ω-hydroxycarboxylic acid through hydrolysis, decarboxylation, and subsequent reduction of the carbonyl group. The present invention relates to a method for producing a long-chain ω-hydroxycarboxylic acid, which is an intermediate to macrocyclic lactones, and 2-(ω-alkoxycarbonyl alkanoyl)-4-butanolide, which is an intermediate to said acid.

Conventionally, there have been many known methods to synthesize long-chain ω-hydroxycarboxylic acids such as 15-hydroxypentadecanoic acid and 16-hydroxyhexadecanoic. An example is the method disclosed in Dutch Patent 67, 458 (1951) [Polak and Schwarz] C. A. 45 9076 (1951). This method, however, needs as many as ten steps to produce a long-chain ω-bromoxylic acid, which is hydrolyzed into a long-chain ω-hydroxycarboxylic acid. This cannot provide a satisfactory industrial process because of the need for many steps for synthesis, relatively low availability of material substances, and hence, unsuitability for industrial mass-production.

Another known method is disclosed in Japanese Patent Laid-Open (Kokai) HEI 5-86013, which uses a ω-cyano fatty ester and γ-butyrolactone as starting materials. Specifically, 11-methyl cyanoundecanoate reacts with γ-butyrolactone in the presense of an alkali metal alcoholate to produce α-(11-cyanoundecanoyl)-γ-butyrolactone, which is then hydrolyzed into 15-hydroxy-12-ketopentadecanonitrile, followed by isolation, secondary hydrolysis, and reduction to provide 15-hydroxypentadecanoic acid.

This method, though being a good one, is still not sufficiently satisfactory because many of the starting materials are not readily available and also because 11-methyl cyanoundecanoate, which is relatively high in price, has to be used as a material. Another problem, though not very serious, is that the nitrile group at the ω-position has to be converted finally into a carboxyl group.

SUMMARY OF THE INVENTION

The objective of the invention is to provide an industrially advantageous method for producing 2-(ω-alkoxycarbonyl alkanoyl)-4-butanolide, which eventually makes it possible to produce a long-chain ω-hydroxycarboxylic acid through a short process and from highly available materials. Another objective is to provide an industrially advantageous method for producing a long-chain ω-hydroxycarboxylic acid.

The present inventors have reached the invention after earnest studies which show that 2-(ω-alkoxycarbonyl alkanoyl)-4-butanolide can be produced unexpectedly with a high selectivity and yield through condensation reacting of γ-butyrolactone with a readily available, low-price dicarboxylate as represented by the following general formula: $ROOC(CH_2)_nCOOR$ (where n denotes an integer of 7 to 13, and R denotes an alkyl or an alkenyl group). The present inventors have established an industrially advantageous method for producing a long-chain ω-hydroxycarboxylic acid after finding that a long-chain ω-hydroxycarboxylic acid is produced by subjecting 2-(ω-alkoxycarbonyl alkanoyl)-4-butanolide to hydrolysis and decarboxylation and reducing the carbonyl groups in the resultant product into methylene groups.

The molecule of a typical long-chain dicarboxylate as used for the present invention contains two functional ester groups connected through a long methylene chain. Therefore, long-chain dicarboxylate is largely different from such compounds as oxalates that contain two functional ester groups located close to each other, which easily undergo such side reactions as self-condensation and intramolecular crosslinking (Dieckmann condensation; J. P. Schaefer, Organic Reactions, Vol.15, p.1, John Wisely & Sons, 1967).

It is expected therefore that only a poorly-practical, low-selectivity method can be formed if an attempt is to be made to obtain a specific condensate through condensation of different esters such as long-chain dicarboxylate and mono-carboxylate (including lactone, which is an intramolecular ester). The inventors have found that the same results are generated from reactions of γ-butyrolactone with adipate, a dicarboxylate that consists of a relatively small number of carbon atoms. They also found, however, that when γ-butyrolactone and a dicarboxylate with 9–15 atoms are used as monocarboxylate and dicarboxylate, respectively, selective condensation takes place on one of the esters in the long-chain dicarboxylate at the α-position of γ-lactone to form 2-(ω)-alkoxycarbonyl alkanoyl)-4-butanolide with a high yield, contrary to the above expectation.

As widely known, long-chain dicarboxylic acid is low in price and widely available as a material for high-quality nylons such as nylon 612 and nylon 610, and therefore long-chain dicarboxylates can also be obtained easily at low cost.

Most Preferred Embodiments of the Invention

For the present invention, condensation of the γ-lactone should be performed in the presense of a condensation agent consisting of a base. Such condensation agents as used herein are those generally used for Claisen condensation and Dieckmann condensation of esters, including alkali metals such as lithium, sodium, and potassium; alkali metal hydrides such as lithium hydride, sodium hydride, and potassium hydride; alkali metal salts of ammonium such as lithium amide, sodium amide, and potassium amide; alkali metal amides of amines such as lithium di-isopropyl amide, sodium di-isopropyl amide, lithium N-methylanilide, and sodium N-methylanilide; magnesium salts of amines such as di-isopropylaminomagnesium chloride and N-methylanilinomagnesium chloride; alkali metal alcoholates of alcohols such as sodium methoxide, sodium ethoxide, sodium n-propoxide, sodium iso-propoxide, sodium n-butoxide, and potassium t-butoxide; and organic alkali metal compounds such as sodium naphthalene and triphenylmethylsodium. Preferred condensation agents for the present invention are alkali metal alcoholates as represented by the general formula ROM where R and M denote an alkyl group with 1–4 carbons and an alkali metal, respectively). There are no specific limitations on the amount of a condensation agent to be used for the invention, but the preferred range is 0.1–5 equivalents, more preferably 0.5–3 equivalents, relative to 1 mole of γ-butyrolactone.

There are no specific limitations on the temperature of the condensation reaction, such as the Claisen condensation, but the preferred range is 0–200° C., more preferably 50–150° C. to produce the alkali metal salt of 2-(ω-alkoxycarbonyl)-4-butanolide.

A dicarboxylate as used for the present invention should be used in an amount that is excessive in moles relative to γ-butyrolactone, preferably two times its amount in moles. The use of a two-fold amount in moles is very effective to increase the selectivity. Recovery of unreacted dicarboxylate from the reaction product and its recycling for the condensation are preferred for increased reaction efficiency. Such recovery of unreacted dicarboxylate from the reaction product can be achieved easily by simple distillation. The use of dicarboxylate in an excessive amount in moles, coupled with its recycling, serves to further increase the reaction efficiency.

It is not essential to use a solvent, but a solvent widely used in ester condensation may be employed in the reaction as long as said solvent does not reduce the activity of the condensation agent. Group R contained in an ester of the general formula $ROOC(CH_2)_nCOOR$ as used for the present invention should be an alkyl group or an alkenyl group. Alkyl groups and alkenyl consisting of 1–6 carbons are preferred because of ease of use. Specifically, such groups for R include methyl, ethyl, propyl, butyl, iso-butyl, pentyl, hexyl, 2-ethylhexyl, octyl, allyl, 2-butenyl, and 2-hexenyl, with methyl particularly preferred.

Methods for producing a long-chain ω-hydroxycarboxylic acid as proposed herein are described below. A long-chain ω-hydroxycarboxylic acid can be easily produced by hydrolyzing the 2-(ω-alkoxycarbonyl alkanoyl)-4-butanolide obtained through the above-mentioned condensation while removing the carbonyl carbon in the lactone portion through decarboxylation, followed by reduction of the carbonyl group in the resultant product into a methylene group. The reaction path is as described below.

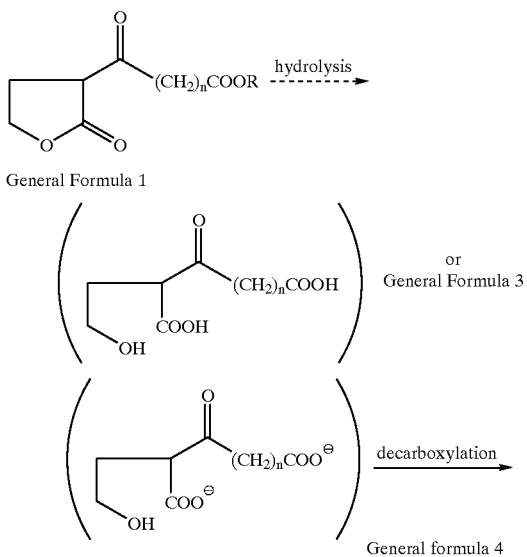

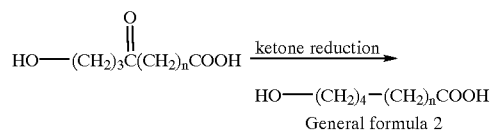

A product as expressed by General formula 3 (where n is an integer of 7–13) is produced as an intermediate when a compound as expressed by General formula 1, namely 2-(ω-alkoxycarbonyl alkanoyl)-4-butanolide, is hydrolyzed by an alkaline base or an acid in an aqueous solution. The compound of General formula 3 immediately undergoes decarboxylation and is converted into a compound as expressed by General formula 4 (where n is an integer of 7–13). Though we have not isolated the compound of General formula 3 for confirmation, it would be obvious that a compound as expressed by General formula 3 is formed in this reaction. When an alkaline base is used for the hydrolysis, the carboxyl groups in the intermediates of General formulae 3 and 4 will be in the form of carboxylates dissolved in the solvent. Any alkaline base that can hydrolyze a lactone and an ester may be used for hydrolyzing the compound of General formula 1, but useful ones include alkali hydroxides such as lithium hydroxide, sodium hydroxide, and potassium hydroxide; alkali metal carbonates such as sodium carbonate and potassium carbonate; and alkaline earth metal hydroxides such as barium hydroxide. Preferred acids include mineral acids such as sulfuric acid. Any widely known reaction that reduces a ketone into a methylene can be used for reducing the ketone in the compound of General formula 4 into a methylene.

An example is the production of a hydrazone through a reaction with a hydrazine, followed by heating with a base to achieve ketone-to-methylene reduction. Useful processes include the Huang-Minlon's improved processes [Huang-Minlon, J. Am. Chem. Soc., 68, 2487 (1946)] which are generally called Wolff-Kishner reduction (David Todd, Organic Reactions, Vol.4, p.378, John Wiley & Sons, 1948).

Such a hydrazone may not be separated, but may be treated with the base after its formation in the reaction system.

Useful bases include alkali metal hydroxides such as sodium hydroxide and potassium hydroxide; alkali metal carbonates such as sodium carbonate and potassium carbonate; alkali metal aluminates such as sodium aluminate and potassium aluminate; alkali metal phosphates such as sodium phosphate and potassium phosphate; alkali metal acetates such as sodium acetate and potassium acetate; and alkali metal alcoholates such as sodium methoxide.

The preferred temperature range is 150–250° C. The molar amount of the hydrazine used should preferably be equal to or greater than, more preferably one to three times, that of the compound of General formula 4. Preferred hydrazines include hydrazine hydrate and hydrazine sulfate.

Other useful methods for reducing a ketone into a methylene include the use of an acid in combination with zinc or a zinc amalgam, such reduction processes being generally called a Clemmensen reduction [E. L. Martin, Organic Reactions, Vol.1, p.155, John Wiley & Sons, (1942)].

The use of a hydrazine is most preferable for the present invention.

To convert the compound of General formula 1 into ω-hydroxycarboxylic acid, the intermediate, i.e. the compound of General formula 4 resulting from hydrolysis, or the reaction mixture containing said intermediate may be subjected directly to the subsequent ketone reduction process, instead of separating or isolating the compound of General formula 4, to produce ω-hydroxycarboxylic acid. It is possible, however, to isolate the compound of General formula 4. For example, the compound of General formula 1 may be hydrolyzed and decarboxylated in an aqueous alkali to produce a reaction mixture containing the compound of General formula 4 (here, the compound of General formula 4 being in the form of an alkali carboxylate), to which a hydrazine is added to form a hydrazone, followed by heating up to a required temperature and implementation of ketone reduction under the existence of a base to obtain an alkali base solution that contains the compound of General formula 2. Then, ω-hydroxycarboxylic acid can be liberated by acidifying this mixture. Needless to say, the present invention is not limited to the processes described above. Furthermore, the compound of General formula 1 may not be isolated during the reaction, but the reaction mixture containing the compound of General formula 1 may be subjected directly to the reaction to produce ω-hydroxycarboxylic acid of General formula 2. A macrocyclic lactone can be produced easily from ω-hydroxycarboxylic acid of General formula 2 through intramolecular cyclization caused by such processes as high-degree dilution, polymerization/depolymerization, and intramolecular ester exchange.

Not only from pure ω-hydroxycarboxylic acid of General formula 2 produced by the method of the present invention, but also from the as-obtained product containing ω-hydroxycarboxylic acid as main component, which is produced by performing the reaction without separating and refining the intermediates of General formulae 1 and 4, a macrocyclic lactone can be easily formed by carrying out cyclization.

The invention is further explained with reference to examples below. The examples, however, are only exemplary of the methods of the invention, and they are not intended to place any limitation on the invention.

EXAMPLE 1

1,12-Dodecanedioic acid dimethyl ester (55.7 g, 216 mmole), γ-butyrolactone (4.3 g, 50 mmole), and sodium (1.20 g, 52 mmole) were mixed at room temperature and heated while being stirred at 110–115° C. for 2 hours in a Claisen condensation reaction to produce

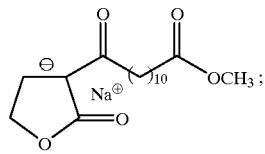

After cooling and adding excessive methanol, the mixture was poured into diluted hydrochloric acid and extracted with ethyl acetate. The organic layer was washed with water and dried over anhydrous magnesium sulfate, followed by distillation of the solvent. The remaining oily matter was distilled under reduced pressure (oil bath temperature 170–180° C., 0.5–0.2 mmHg), followed by distillation of the excessive 1,12-dodecanedioic acid dimethyl ester. A fraction of 42.17 g and a distillation residue of 14.48 g were obtained. A 6 g portion of the distillation residue was taken and developed using benzene/ethyl acetate mixture solvent for silica gel column chromatography, thus producing 4.13 g of a compound of General formula 1 (n=10, R=Me).

This compound was recrystallized from an ether/hexane mixture to provide 3.42 g of the compound of General formula 1 (n=10, R=Me) with a melting point of 43–45° C. IR, NMR, and mass-spectral measurements were carried out to confirm that the compound actually had the structure represented by General formula 1 (n=10, R=Me).

| Elemental analysis | C | H |
|---|---|---|
| Calculation for $C_{17}H_{38}O_5$ (%) | 65.36 | 9.03 |
| Measurement (%) | 65.53 | 8.99 |

Gas chromatography analysis was performed for the distillation residue, revealing that it contains 68 wt. % of the compound of General formula 1 (n=10, R=Me). The yield based on γ-butyrolactone was 64%.

EXAMPLE 2

1,12-Dodecanedioic acid dimethyl ester (55.7 g, 216 mmole), γ-butyrolactone (4.3 g, 50 mmole), and sodium methoxide (2.81 g, 52 mmole) were mixed at room temperature and heated while being stirred at 110–115° C. for 2 hours. After the same post-treatment as in Example 1, a fraction of 43.26 g and a distillation residue of 13.91 g were obtained. Analysis was performed for the distillation residue, revealing that it contains 69 wt. % of the compound of General formula 1 (n=10, R=Me). The yield based on γ-butyrolactone was 62%.

The procedure was carried out for sodium hydride and sodium amide instead of sodium methoxide, and reaction was performed with the same molar composition and under the same reaction conditions. Results showed that the yield of the compound of General formula 1 (n=10, R=Me) was 65% and 57% when sodium hydride and sodium amide were used, respectively.

EXAMPLE 3

Reaction was performed under the same conditions except that 60 ml of toluene was added as solvent. The yield of the compound of General formula 1 (n=10, R=Me) was 56%.

EXAMPLE 4

1,12-Dodecanedioic acid dimethyl ester (30.96 g, 120 mmole), γ-butyrolactone (42.58 g, 120 mmole), and sodium methoxide (1.69 g, 30 mmole) were mixed at room temperature and heated while being stirred at 110° C. for 2 hours while removing methanol. After the same post-treatment and distillation procedure as in Example 2, a fraction of 23.63 g and a distillation residue of 8.36 g were obtained. Analysis was performed for the distillation residue, revealing that it contains 85.1 wt. % of the compound of General formula 1 (n=10, R=Me). The yield was 62%, and the selectivity was 77%. When the same reaction was performed without removing the methanol resulting from the reaction, the yield was 62%, and the selectivity was 63%.

The same reaction was performed with 60 mmole or 180 mmole of 1,12-dimethyl ester of dodecanedioic acid.

In the former case, the yield was 62% and the selectivity was 70% when methanol removal was conducted during the reaction, while the yield was 49% and the selectivity was 56% when methanol removal was not conducted during the reaction. In the latter case, the yield was 79% and the selectivity was 79% when methanol removal was conducted during the reaction, while the yield was 65% and the selectivity was 66% when methanol removal was not conducted during the reaction.

EXAMPLE 5

1,13-tridecanedioic acid dimethyl ester (=brassilic acid dimethyl ester) (65.2 g, 200 mmole), γ-butyrolactone (4.3 g, 50 mmole), and metallic sodium (1.20 g, 52 mmole) were mixed at room temperature and heated while being stirred at 110–115° C. for 2 hours. After cooling and adding excessive methanol, the mixture was poured into diluted hydrochloric acid and extracted with ethyl acetate. The organic layer was washed with water and dried over anhydrous magnesium sulfate, followed by distillation of the solvent. The remaining oily matter was distilled under reduced pressure (oil bath temperature 180–200° C., 0.5–0.2 mmHg), followed by distillation of the excessive brassilic acid dimethyl ester. The residue was heated, and a 4.2 g of fraction of a compound of General formula 1 (n=11, R=Me) with a boiling point of 209–213° C./$10^{-2}$ mmHg was obtained. It was further refined by column chromatography, separating 9.8 g of the compound of General formula 1 (n=11, R=Me).

IR, NMR, and mass-spectral measurements were carried out to confirm the structure. The yield based on γ-butyrolactone was 60%.

| Elemental analysis | C | H |
|---|---|---|
| Calculation for $C_{18}H_{30}O_5$ (%) | 66.24 | 9.26 |
| Measurement (%) | 66.51 | 9.12 |

EXAMPLE 6

1,12-Dodecanedioic acid dimethyl ester (55.7 g, 216 mmole), γ-butyrolactone (4.3 g, 50 mmole), and metallic sodium (1.20 g, 52 mmole) were reacted by the same procedure as in Example 1.

The excessive 1,12-dodecanedioic acid dimethyl ester was distilled out, leaving 14.50 g distillation residue consisting mainly of a compound of General formula 1 (n=10, R=Me) (content: 72 wt. %). The residue was mixed with 150 g of methanol and 300 g of aqueous solution of sodium hydroxide, followed by heating at reflux for 5.5 hours. The material was aspirated with an aspirator until ⅔ of the methanol and water were distilled off. Then, 80 ml of diethylene glycol and 6.5 ml of 85% hydrated hydrazine were added to the residue, which was then heated while being stirred at 110° C. for 1 hour, followed by heating up to 195–200° C. and stirring at the temperature for 14 hours. After cooling, diluted hydrochloric acid was added, and extraction was performed with chloroform. After-treatment was conducted to produce 13.7 g of crystalline residue containing 15-hydroxypentadecanoic acid 2 (n=10) as main component. Cyclization was carried out through intramolecular transestrification to provide 5.18 g of crude cyclopentadecanolide, which contained 97 wt. % cyclopentadecanolide.

EXAMPLE 7

1,13-tridecanedioic acid dimethyl ester (=brassilic acid dimethyl ester) (65.2 g, 200 mmole), γ-butyrolactone (4.3 g, 50 mmole), and metallic sodium (1.20 g, 52 mmole) were reacted as in Example 5. After the completion of the reaction, the excess amount of brassilic acid dimethyl ester was distilled off, producing 15.3 g of distillation residue containing a compound of General formula 1 (n=11, R=Me) as main component. It was mixed with 150 g of methanol and 300 g of 4% aqueous solution of sodium hydroxide, followed by heating at reflux for 5.5 hours. Then the same procedure as in Example 6 was performed for hydrazine reduction to provide 14.4 g of a crystalline product containing 16-hydroxyhexadecanoic acid 2 (n=11), followed by cyclization to form 5.17 g of crude cyclohexadecanolide. It was refined to provide pure cyclohexadecanolide, which had the same spectral and physical properties as the standard sample.

EXAMPLE 8

1,12-dodecanedioic acid dimethyl ester (55.7 g, 216 mmole), γ-butyrolactone (4.3 g, 50 mmole), and metallic sodium (1.20 g, 52 mmole) were reacted by the same procedure as in Example 6, followed by post-treatment to produce 13.2 g of a crystalline residue containing 15-hydroxypentadecanoic acid 2 (n=10) as main component. Gas chromatography showed that the residue contained 61 wt. % of 15-hydroxypentadecanoic acid 2 (n=10).

EXAMPLE 9

1,10-decanoic acid dimethyl ester (sebacic acid dimethyl ester) (49.7 g, 216 mmole), γ-butyrolactone (4.3 g, 50 mmole), and sodium (1.20 g, 52 mmole) were reacted by the same procedure as in Example 6, followed by post-treatment to produce 11.7 g of a crystalline residue containing 13-hydroxytridecanoic acid 2 (n=8) as main component. It was recrystallized and subjected to gas chromatography to isolate 13-hydroxytridecanoic acid. Its melting point was 77–78° C. Its structure was confirmed from IR and NMR spectral observation.

| Elemental analysis | C | H |
|---|---|---|
| Calculation for $C_{13}H_{26}O_3$ (%) | 67.75 | 11.38 |
| Measurement (%) | 67.81 | 11.36 |

Gas chromatography showed that the above-mentioned residue contained 60% 13-hydroxytridecanoic acid 4 (n=8).

COMPARATIVE EXAMPLE 1

Adipic acid dimethyl ester (17.4 g, 100 mmole), γ-butyrolactone (2.15 g, 25 mmole), and sodium methoxide (1.41 g, 25 mmole) were mixed at room temperature and heated while being stirred at 110° C. for 2 hours while removing methanol. After the same post-treatment and distillation procedure as in Example 1 to distill off the adipic acid dimethyl ester. The distillation residue of 8.36 g was subjected to silica gel chromatography and developed with a benzene/ethyl acetate (11:1) mixture solvent to provide 0.46 g of a compound of General formula 1 (n=4, R=Me). The yield was 8%.

EXAMPLE 10

A compound of General formula 1 (n=10, R=Me) (8.37 g, 26.8 mmole), 170 g of aqueous solution of sodium hydroxide, and 83 g of methanol were mixed and heated at reflux for 6 hours, followed by hydrolysis and decarboxylation.

Diluted hydrochloric acid, ice, and chloroform were poured in a separating funnel, and the above-mentioned mixture is added to this, immediately followed by extraction. The chloroform layer was rinsed, and dried with anhydrous magnesium sulfate, and the solvent was distilled off to provide a crystalline material, followed by recrystallization from a ether/hexane mixture to produce 6.7 g of a compound of General formula 4 (n=10). Its melting point was 77–78° C., and its structure was confirmed from IR and NMR spectral observation.

| Elemental analysis | C | H |
| --- | --- | --- |
| Calculation for $C_{15}H_{28}O_4$ (%) | 66.14 | 10.36 |
| Measurement (%) | 66.24 | 10.02 |

EXAMPLE 11

A compound of General formula 1 (n=10, R=Me) (150 g, 4.81 mmole) and 20 g of 3% sulfuric acid were mixed and heated while being stirred for 6 hours. Ice and chloroform were added, followed by extraction. The chloroform layer was washed with water, and dried over anhydrous magnesium sulfate, and the solvent was distilled off to provide a crystalline material. It was trimethylsililated, and the product was analyzed by gas chromatography. Results showed that a compound of General formula 1 (n=10) had been formed with a yield of 38%.

EXAMPLE 12

A compound of General formula 4 (n=10) (2.72 g, 10 mmole) was mixed with 2.0 g of ground sodium hydroxide, 16 ml of diethylene glycol, 1.3 ml of 85% hydrated hydrazine, and 0.6 ml of methanol, and stirred at 110° C. for 30 min. The mixture was heated up to 195–200° C. and stirred for 15 hours. Distillable components were completely distilled off to ensure its removal out of the system. The residue was cooled, acidified and subjected to extraction with chloroform. The chloroform layer was washed with water, and dried over anhydrous magnesium sulfate, and the solvent was distilled off to provide a crystalline material. It was recrystallized from benzene to produce 2.1 g of 15-hydroxypentadecanoic acid 2 (n=10). The yield was 81%. The product had a melting point of 84–86° C. The structure of 15-hydroxypentadecanoic acid was confirmed from IR and NMR spectral observation.

| Elemental analysis | C | H |
| --- | --- | --- |
| Calculation for $C_{15}H_{30}O_3$ (%) | 69.72 | 11.70 |
| Measurement (%) | 69.85 | 11.57 |

EXAMPLE 13

A compound of General formula 1 (n=10, R=Me) (2.00 g, 6.41 mmole), aqueous solution of sodium hydroxide (1.75 g, 43.7 mmole), 40 g of water, and 20 g of methanol were mixed and heated at reflux for 4 hours. The oil bath was maintained at 130° C. to distill of about a half of the methanol and water. After the distillation, 11 ml of diethylene glycol was added, and distillation was continued for 1 hour. Then, 101 ml of 85% hydrated hydrazine was added and stirred at 110° C. for 40 min. The system was heated up to 195–200° C. and stirred at the temperature for 16 hours, followed by the same post-treatment procedure as in Example 12 to produce 1.57 g of crystalline material. The material was trimethylsililated and the product was subjected to analysis by gas chromatography. Results showed that it contained 99% 15-hydroxypentadecanoic acid 2 (n=10). The yield of the compound of General formula 1 (n=10, R=Me) was 94%.

EXAMPLE 14

Zinc (2.14 g) was mixed with 3.57 ml of water and 0.1 ml of concentrated hydrochloric acid, and mercuric chloride (0.21 g) was added to the mixture, which was shaken well for 5 min to ensure amalgamation. Decantation was carried out to remove the supernatant liquid. To the resultant material, 1.34 ml of water and 3.1 ml of concentrated hydrochloric acid were added, and then 1.5 ml of toluene and a compound of General formula 4 (n=10) (1.36 mmole) were added, followed by heating at reflux for 11 hours, with 1 ml of concentrated hydrochloric acid being added after 6 hours. After the completion of the reaction, water and chloroform were added and extraction was conducted. The chloroform layer was washed with water, and dried over anhydrous magnesium sulfate, followed by distillation of the solvent, leaving 1.10 g of crystalline residue. Gas chromatography showed that the yield of 15-hydroxypentadecanoic acid 2 (n=10) was 51%.

EXAMPLE 15

A compound of General formula 4 (n=10) (1.00 g, 3.68 mmole) was dissolved in 50 ml of methanol, and toluenesulfonyl hydrazide (1.4 g) was added, followed by heating at reflux for 3 hours. To the solution, 1.4 g of sodium borohydride was added little by little while being cooled and stirred, and heating was continued at reflux for 4 hours. After the completion of the reaction, the solution was poured in diluted hydrochloric acid for extraction with chloroform. Post-treatment was performed to produce 1.47 g of residue. Gas chromatography showed that the yield of 15-hydroxypentadecanoic acid 2 (n=10) was 62%.

EXAMPLE 16

A compound of General formula 1 (n=11, R=Me) (2.00 g, 6.13 mmole) was hydrolyzed, decarboxylated, and reduced with hydrazine (1.4 g) to produce 1.59 g of crystalline material containing 16-hydroxyhexadecanoic acid 2 (n=11) as main component. It was recrystallized from benzene to obtain 1.2 g of 16-hydroxyhexadecanoic acid 2 (n=11). It had a melting point of 92–94° C., and its structure was confirmed from IR and NMR spectral observation.

| Elemental analysis | C | H |
| --- | --- | --- |
| Calculation for $C_{16}H_{32}O_3$ (%) | 72.93 | 10.88 |
| Measurement (%) | 73.11 | 10.69 |

What is claimed is:

1. 2-(ω-alkoxycarbonyl-alkanoyl) 4-butanolide having a structure expressed by the formula:

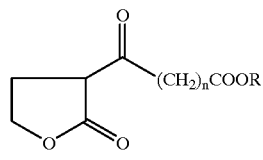

wherein n is 11 and R is an alkyl group having 1–6 carbon atoms.

2. 2-(ω-methoxycarbonyl) 4-butanolide having a structure expressed by the formula:

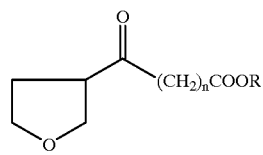

wherein n is 11 and R is a methyl group.

3. 2-(ω-alkoxycarbonyl-alkanoyl) 4-butanolide having a structure expressed by the formula:

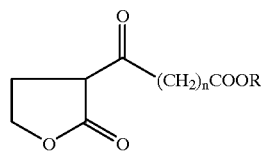

wherein n is 7–9 and R is an alkyl group having 1–6 carbon atoms.

4. 2-(ω-methoxycarbonyl) 4-butanolide having a structure expressed by the formula:

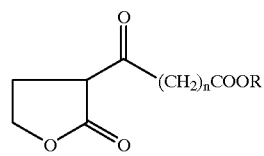

wherein n is 7–9 and R is a methyl group.

5. 2-(ω-alkoxycarbonyl-alkanoyl) 4-butanolide having a structure expressed by the formula:

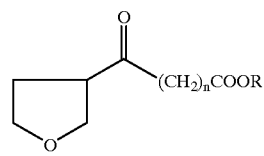

wherein n is 12 or 13 and R is an alkyl group having 1–6 carbon atoms.

6. 2-(ω-methoxycarbonyl) 4-butanolide having a structure expressed by the formula:

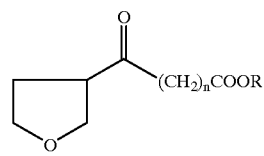

wherein n is 12 or 13 and R is a methyl group.

* * * * *

UNITED STATES PATENT AND TRADEMARK OFFICE
CERTIFICATE OF CORRECTION

PATENT NO.    : 6,222,049 B1
DATED         : April 24, 2001
INVENTOR(S)   : Katou et al.

It is certified that error appears in the above-identified patent and that said Letters Patent is hereby corrected as shown below:

Column 2,
Line 24, please change "loω" to -- low --.

Claims 2, 4, and 6,
Please replace the formula in each claim with the following formula:

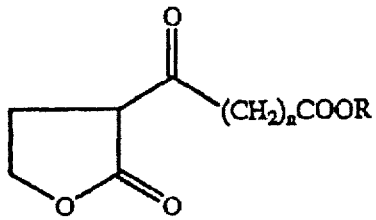

Signed and Sealed this

Nineteenth Day of February, 2002

Attest:

JAMES E. ROGAN
*Attesting Officer*          *Director of the United States Patent and Trademark Office*